United States Patent
Slemker et al.

(10) Patent No.: US 6,228,124 B1
(45) Date of Patent: May 8, 2001

(54) PROSTHETIC FOOT WITH LATERAL AND ANGULAR ADJUSTABILITY

(75) Inventors: Tracy C. Slemker, Clayton; Lanny Wiggins, Miamisburg, both of OH (US)

(73) Assignees: Prosthetic Design, Inc., Clayton; CaTech, Inc., Centerville, both of OH (US)

(*) Notice: Subject to any disclaimer, the term of this patent is extended or adjusted under 35 U.S.C. 154(b) by 0 days.

(21) Appl. No.: 09/149,687

(22) Filed: Sep. 8, 1998

Related U.S. Application Data
(60) Provisional application No. 60/058,214, filed on Sep. 8, 1997.

(51) Int. Cl.$^7$ ..................................................... A61F 2/64
(52) U.S. Cl. ........................................................... 623/47
(58) Field of Search .................................. 623/47, 53, 40, 623/38, 27, 55; 3/500; 403/381, 331

(56) References Cited

U.S. PATENT DOCUMENTS

| | | |
|---|---|---|
| 1,281,191 * | 8/1918 | Michajlov . |
| 3,206,235 | 9/1965 | Albinson et al. ................... 287/21 |
| 3,940,804 * | 3/1976 | Benton et al. ...................... 623/38 |
| 4,007,496 * | 2/1977 | Glabiszewski ...................... 623/47 |
| 4,065,815 * | 1/1978 | Sen-Jung ............................ 3/1.2 |
| 4,132,335 * | 1/1979 | Ingram ............................. 224/42.1 |
| 4,536,898 * | 8/1985 | Palfray ............................... 623/33 |
| 4,636,220 | 1/1987 | Ziegelmeyer ....................... 623/20 |
| 4,923,472 * | 5/1990 | Ugolini ............................. 623/20 |
| 4,969,911 | 11/1990 | Greene .............................. 623/38 |
| 5,047,063 | 9/1991 | Chen ................................. 623/38 |
| 5,425,781 | 6/1995 | Allard et al. ....................... 623/38 |
| 5,443,526 | 8/1995 | Hoerner ............................. 623/38 |
| 5,458,657 | 10/1995 | Rasmusson ........................ 623/38 |
| 5,529,576 | 6/1996 | Lundt et al. ....................... 623/38 |
| 5,545,230 | 8/1996 | Kinsinger et al. ................. 623/38 |
| 5,549,710 * | 8/1996 | Vera et al. ......................... 623/38 |
| 5,653,767 * | 8/1997 | Allen et al. ....................... 623/52 |
| 6,033,440 * | 3/2000 | Schall et al. ...................... 623/38 |

FOREIGN PATENT DOCUMENTS

| | | | |
|---|---|---|---|
| 0667883 * | 8/1965 | (BE) ................................. | 623/38 |
| 638095 | 9/1983 | (CH) . | |
| 3937379 | 9/1989 | (DE) . | |
| 2410998 | 8/1979 | (FR) . | |
| 0978586 * | 12/1964 | (GB) ................................. | 623/38 |
| 2027592 | 8/1978 | (GB) . | |
| 9000418 | 6/1990 | (WO) . | |

OTHER PUBLICATIONS
Prosthetic Design, Inc.–catalog pages of pyramids.

\* cited by examiner

*Primary Examiner*—Dinh X. Nguyen
*Assistant Examiner*—Alvin Stewart
(74) *Attorney, Agent, or Firm*—Thompson Hine & Flory LLP

(57) ABSTRACT

A prosthetic foot comprises: (a) a prosthetic foot member having a fore-foot portion and a heel/ankle portion; (b) a dove-tail shaped anchoring member positioned on a proximal surface of the heel/ankle portion, where the dove-tail shaped anchoring member has a proximal face, and a pair of outwardly angled vertical faces; (c) a pylon support member having an upper end adapted to receive and couple to a pylon component of a prosthetic limb, and a lower end with a dove-tail shaped groove extending therein, where the dove-tail shaped groove has a pair of inwardly angled vertical faces and an inner-distal face, and where the dove-tail shaped anchoring member is slidingly received within the dove-tail shaped groove of the pylon support member; and (d) a threaded coupler cooperative with the dove-tail shaped anchoring member to draw the inwardly angled vertical faces of the pylon support member into an interference fit with the outwardly angled faces of the dove-tail shaped anchoring member, thereby inhibiting sliding of the pylon support member with respect to the dove-tail shaped anchoring member.

24 Claims, 6 Drawing Sheets

PROSTHETIC FOOT WITH LATERAL AND ANGULAR ADJUSTABILITY

CROSS REFERENCE TO RELATED APPLICATIONS

This application claims priority under 35 U.S.C. §19 from provisional application Serial No. 60/058,214, filed Sep. 8, 1997, the entire disclosure of which is incorporated herein by reference.

BACKGROUND

The present invention is directed to a prosthetic foot, and more particularly, to a prosthetic foot that provides both angular and anterior-posterior lateral adjustability with respect to the upright assembly coupled thereto.

A prostheses is often used to replace and amputated portion of a limb and help to restore the amputee's ability to use that limb. A prostheses for a lower extremity amputation will often include an artificial foot connected to an upright assembly (pylon, tube or shaft) which is in turn connected to a custom fitted socket assembly. If the amputation is above the knee, the upright assembly will commonly include an artificial knee joint.

U.S. Pat. No. 5,529,576 discloses a prosthetic foot having a pyramidal link plate mounted within a recess extending into a proximal end of the prosthetic foot. While the pyramidal link plate, in conjunction with the annular socket component coupled to the distal end of the upright assembly, allows for angular adjustments of the upright assembly with respect to the prosthetic foot, this coupling does not provide for any translational adjustments.

While some prosthetists believe that such angular adjustability alone provides sufficient versatility to the prosthetic limb so as to allow the prosthetists to adjust and control heel strike and heel compression of the prosthetic limb, other prosthetists believe that upright assemblies that are substantially angled with respect to the prosthetic foot will adversely affect ground reaction forces during gate. In this case, once the prostheses is aligned, the prosthetists will often prefer to "transfer" the socket and foot to a fixture and thereafter realign the prosthetic components between the socket and the foot to achieve pylon verticality.

Additionally, regardless of the angle of the upright assembly, it is also sometimes desirable to provide for translational adjustment or alignment versatility of the prosthetic foot with respect to the prosthetic limb. Such anterior-posterior translation will affect the patient's and prosthetist's ability to control heel strike and heel compression in modern prosthetic feet. For example, when an energy storing foot is used, when the upright assembly is slid in the posterior direction with respect to the prosthetic foot, this adjustment results in a longer lever arm for toe-off at midstance. In the contrary, when the upright assembly is slid in the anterior direction with respect to the prosthetic foot, this adjustments results in a short lever arm for toe-off at midstance, which in turn means that this alignment may be more stable for a new amputee.

U.S. Pat. No. 4,636,220 discloses a prosthetic foot that provides for heel height adjustment of the foot. The prosthetic foot includes a cavity in the keel of the foot which is shaped and sized to receive a bolt-block extending distally from pylon component of the prosthetic limb. An arcuate rail component is secured to the distal end of the bolt block; and the arcuate rail component engages an arcuate groove and track component securing to the upper surface of the cavity in the foot. Apertures are provided in both the arcuate rail component and the arcuate groove component, and a threaded bolt extends upwardly through the apertures and into a threaded bore in the bolt block. Upon tightening the bolt, the arcuate rail component is fixedly wedged within the arcuate groove component to firmly retain the bolt block in a fixed position within the cavity. To adjust the heel height (vertical/angular adjustment), the bolt is loosened, the arcuate rail is slid forward or backward within the groove depending upon the desired adjustment, and then the bolt is tightened again when the arcuate rail and bolt block are in the desired orientation. A disadvantage of this system is that the design dictates that lateral adjustments must occur with the vertical/angular adjustments—independent lateral or vertical/angular adjustments are not provided. Further, to make such adjustments with this system, the cosmetic cover of the prosthetic limb must be removed after each adjustment to maintain pylon verticality. Finally, this system requires a specially designed prosthetic foot and is not capable of being used on conventional, industry standard, prosthetic foot components.

Accordingly, there is a need for a prosthetic foot interconnection assembly which provides for independent lateral and angular adjustments; which allows for independent translational adjustments, yet which in turn, does not adversely affect the pylon verticality; which provides for lateral adjustments, especially anterior-posterior adjustments; which does not require that the prosthetic limb be disassembled or even removed from the patient's residual limb during or before adjustment; which is easy to assemble and adjust; which may be used with conventional, industry standard, prosthetic foot components; and which is relatively easy and inexpensive to manufacture.

SUMMARY

The present invention provides a prosthetic foot that comprises a prosthetic foot member having a fore-foot portion and a heel/ankle portion; a dove-tail shaped anchoring member positioned on a proximal surface of the heel/ankle portion, where the dove-tail shaped anchoring member has a proximal face, and a pair of outwardly angled vertical faces; and a pylon support member having a proximal end adapted to receive and couple to a pylon component of a prosthetic limb. The pylon support member includes a dove-tail shaped groove extending into the bottom face thereof, where the dove-tail shaped groove has a pair of inwardly angled vertical faces and an inner-distal face. The dove-tail shaped anchoring member is slidingly received within the dove-tail shaped groove of the pylon support member. The prosthetic foot also comprises a threaded coupler cooperative with the dove-tail shaped anchoring member to draw the inwardly angled vertical faces of the pylon support member into an interference fit with the outwardly angled faces of the dove-tail shaped anchoring member, thereby inhibiting sliding of the pylon support member with respect to the dove-tail shaped anchoring member.

Preferably the threaded coupler includes a threaded bore extending vertically into the distal face of the dove-tail shaped anchoring member and a correspondingly threaded bolt for extending upwardly into the threaded bore. The prosthetic foot includes a non-threaded bore extending vertically therethrough, which is aligned with the threaded bore of the dove-tail shaped anchoring member and provides access for the prosthetist to the threaded bolt from the distal end of the heel/ankle portion of the prosthetic foot. The non-threaded bore in the prosthetic foot includes a shoulder for seating a head of the threaded bolt. Accordingly, as the threaded bolt is extended through the bore in the prosthetic foot and threaded into the threaded bore in the distal end of the dove-tail shaped anchoring member, the shoulder will prohibit the bolt to translate in a proximal direction (vertically upward). Thus, further turning of the threaded bolt causes the dove-tail shaped anchoring member to be drawn distally towards the prosthetic foot. This causes the dove-tail shaped anchoring member to be pressed away from the pylon support member, which causes the inwardly angled vertical faces of the pylon support member to press against the outwardly angled faces of the dove-tail shaped anchoring member, thereby inhibiting sliding of the pylon support member with respect to the dove-tail shaped anchoring member.

Accordingly, to adjust the prosthetic foot laterally with respect to the upright assembly, the prosthetists will merely need to loosen the bolt, slide the prosthetic foot laterally with respect to the upright assembly to the desired position, and then tighten the bolt again. Because the bolt is accessible through the distal end of the prosthetic foot, the prosthetic limb will not have to be removed from the patient during such adjustments.

Another aspect of the invention is directed to a prosthetic foot that comprises: (a) a prosthetic foot member; (b) an anchoring member positioned on a proximal surface of the heel-ankle portion of the prosthetic foot member, where the anchoring member has a proximal face, and a pair of outwardly extending faces; (c) a pylon support member adapted to receive and couple to a pylon component of a prosthetic limb, having a groove extending into the bottom face of the pylon support member, where the groove has a pair of inwardly extending faces and an inner distal face, and where the anchoring member is slidingly received within the groove of the pylon support member such that the outwardly extending faces of the anchoring member are juxtaposed with the inwardly extending faces of the groove; and (d) a threaded coupler cooperative with the anchoring member to draw the inwardly extending faces of the pylon support member into an interference fit with the outwardly extending faces of the anchoring member, thereby inhibiting sliding of the pylon support member with respect to the anchoring member.

Another aspect of the present invention is directed to a prosthetic limb that comprises a prosthetic foot; a pylon support member slidably mounted to a proximal end of the prosthetic foot, where the pylon support member has a domed portion and a frustopyramidal boss portion extending from the dome portion, where the frustopyramidal boss portion has a least two opposing, outwardly angled faces, and where the pylon support member is slidable in the anterior-posterior direction; an upright assembly adapted to extend from a distal end of a patient's residual limb, where the upright assembly includes an annular socket member at a distal end thereof, where the annular socket member includes at least two diametrically opposed set screws extending radially into a central bore of the annular socket member, where the set screws are angled proximally, and where the frustopyramidal boss portion of the pylon support member is received within the central bore of the annular socket member and the set screws are tightened against the opposing faces of the frustopyramidal boss portion, thereby coupling the upright assembly to the pylon support member and the prosthetic foot; and a releaseable lock, adapted to inhibit sliding of the pylon support member with respect to the prosthetic foot in the anterior-posterior direction when in a locked orientation.

Yet another aspect of the present invention is directed to a link plate assembly for adjustably coupling a first prosthetic limb component to a second prosthetic limb component that comprises: (a) a dove-tail shaped anchoring member having a top face, and a pair of outwardly angled vertical faces; (b) a pylon support member having an upper end adapted to receive and couple to a pylon component of a prosthetic limb, and a dove-tail shaped groove extending into the bottom face, where the dove-tail shaped groove has a pair of inwardly angled vertical faces in an inner bottom face, and where the dove-tail shaped anchoring member is slidingly received within the dove-tail shaped groove of the pylon support member; and (c) a threaded press cooperative with the dove-tail shaped anchoring member to draw the inwardly angled vertical faces of the pylon support member into an interference fit with the outwardly angled faces of the dove-tail shaped anchoring member, thereby inhibiting sliding of the pylon support member with respect to the dove-tail shaped anchoring member.

Preferably, the threaded press includes a threaded bore extending vertically into the distal face of the dove-tail shaped anchoring member and a correspondingly threaded bolt for extending upwardly into the threaded bore. Such a threaded press operates with the conventional prosthetic foot, described above, which includes a non-threaded bore extending vertically therethrough, and which is aligned with the threaded bore of the dove-tail shaped anchoring member and provides access for the prosthetist to the threaded bolt from the distal end of the heel/ankle portion of the prosthetic foot.

Alternatively, the threaded press includes a threaded bore extending vertically through the dove-tail shaped anchoring member and a correspondingly threaded bolt extends upwardly through the threaded bore. Therefore, upon rotation of the bolt in a first direction, the bolt translates upwardly, causing the end of the bolt to press against the inner bottom face of the pylon support member, which pushes the top face of the dove-tail shaped anchoring member away from the inner bottom face in the dove-tail shape groove of the pylon support member, and which in turn causes the inwardly angled vertical faces of the pylon support member to press against the outwardly angled faces of the dove-tail shaped anchoring member, thereby inhibiting sliding of the pylon support member with respect to the dove-tail shaped member. Upon rotation of the bolt in the opposite direction, the bolt translates downwardly, which allows the pylon support member to slide again with respect to the dove-tail shaped anchoring member.

Accordingly, it is an object of the present invention to provide a prosthetic foot which allows lateral adjustments, especially anterior-posterior adjustments, without substantially affecting the verticality of the upright assembly; it is an object of the present invention to provide a prosthetic foot and associated link plate assembly where such lateral adjustments may be made without requiring the prosthetic limb to be removed from the patient's residual limb; and it is a further object of the present invention to provide a prosthetic foot having such lateral adjustability that is easy and inexpensive to manufacture. These and other objects of the present invention will be apparent from the following description, the appended claims and the attached drawings.

DETAILED DESCRIPTION

Figure 1:
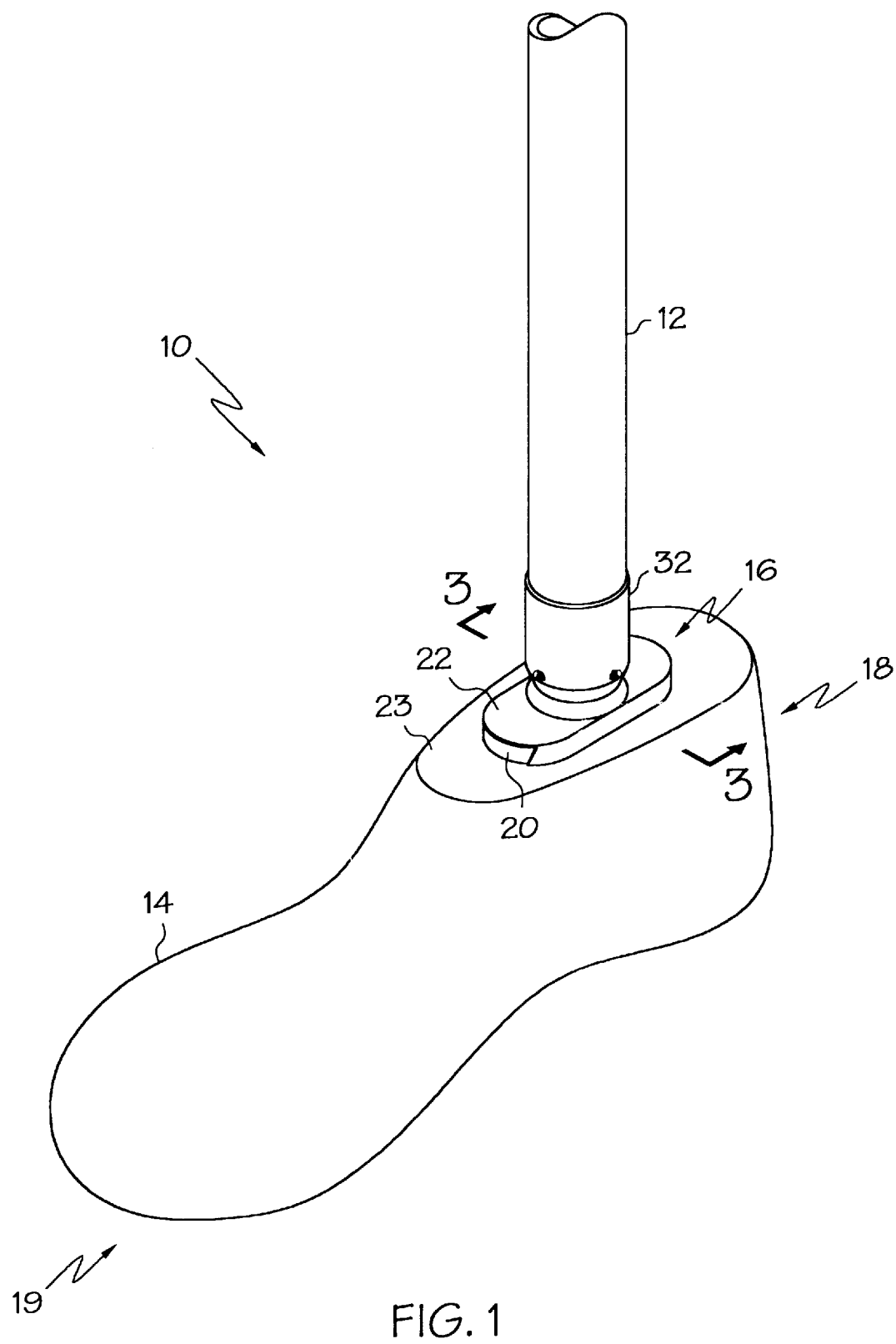
FIG. 1 is a perspective view of a prosthetic foot component of the present invention coupled to an upright assembly of a prosthetic limb.
Figure 2:
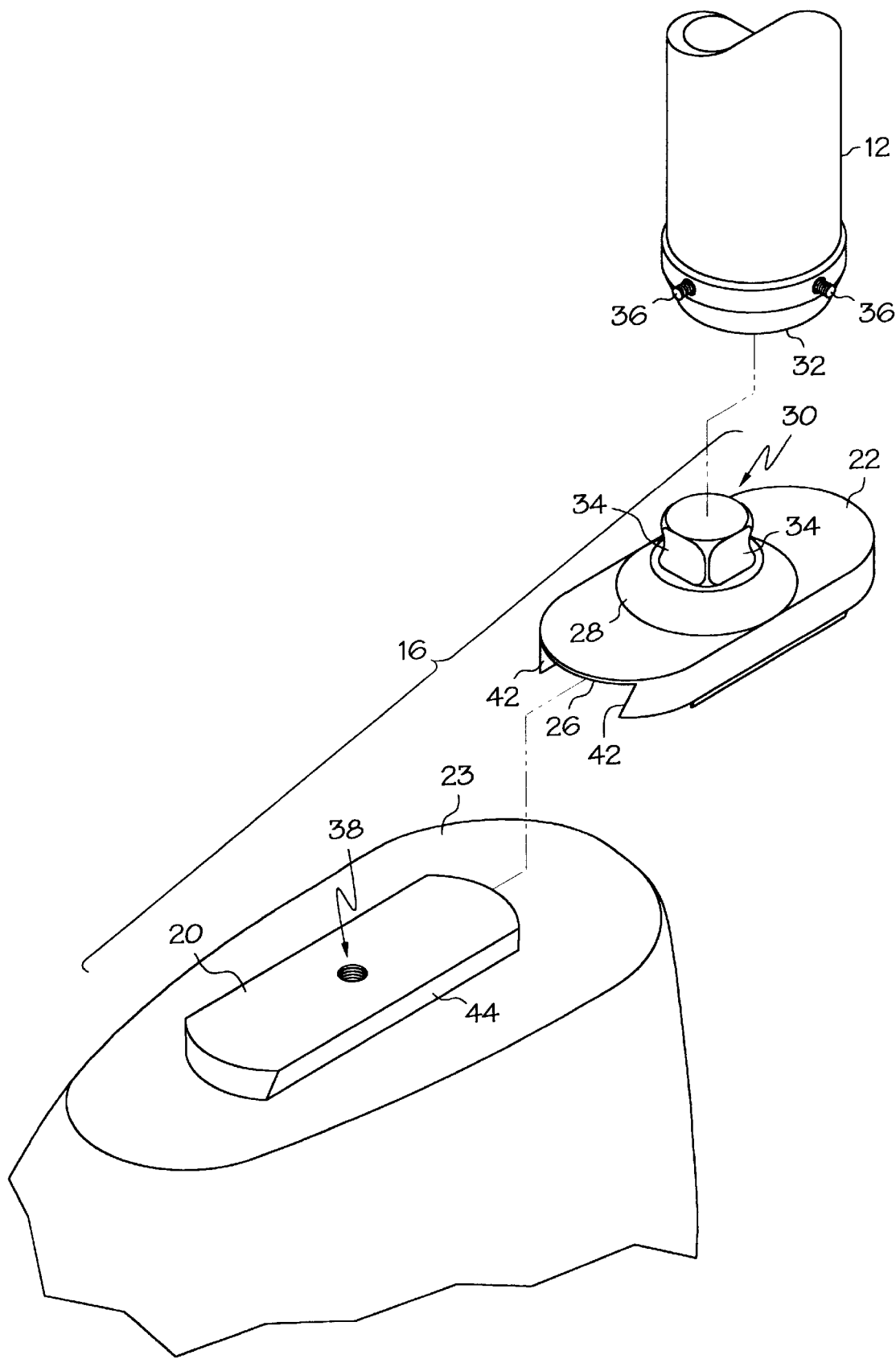
FIG. 2 is an exploded, magnified, and perspective view of the prosthetic foot, link plate assembly and upright assembly of FIG. 1.
Figure 3:
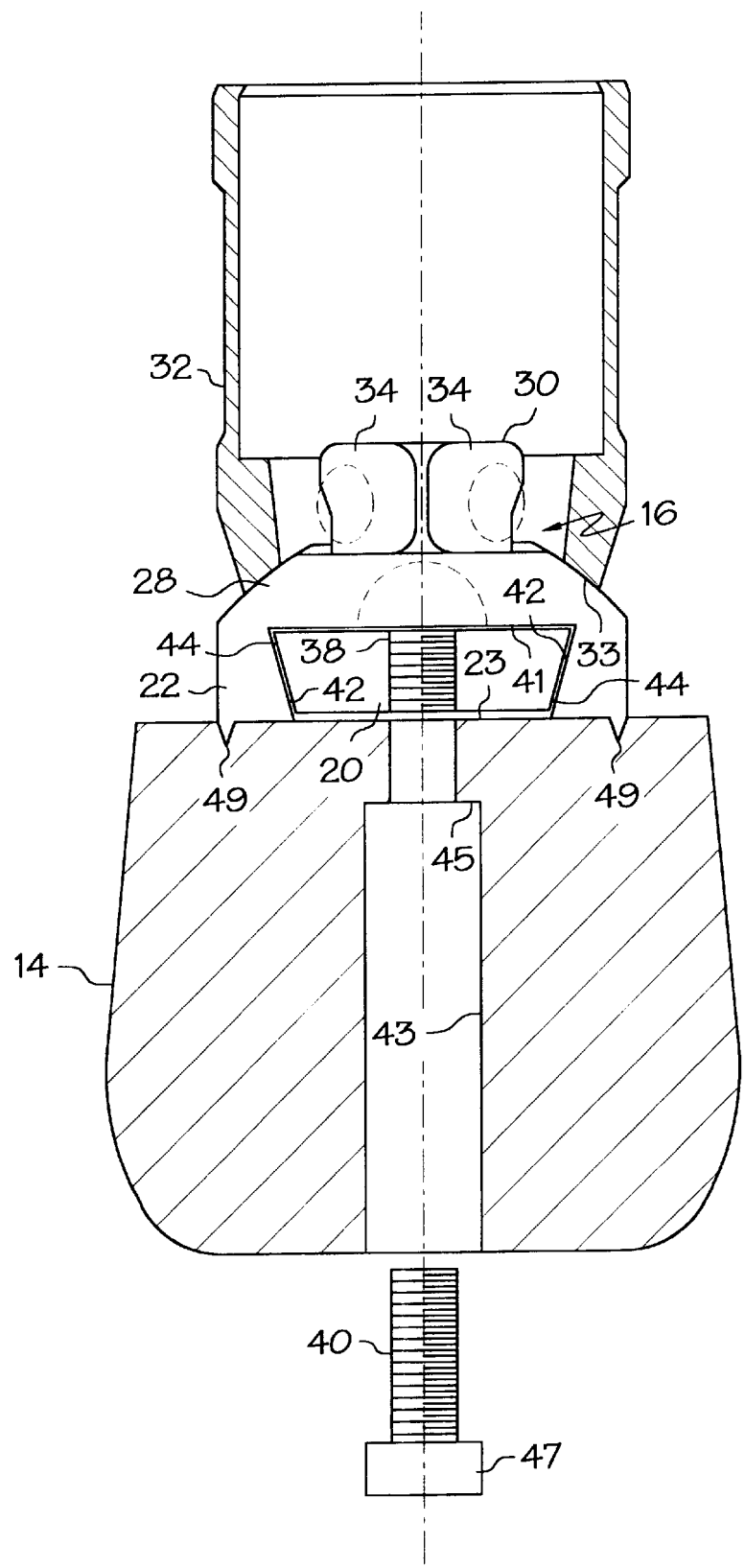
FIG. 3 is an elevational, cross-sectional view of the prosthetic foot and upright assembly of FIG. 1 taken along lines 3—3 of FIG. 1.

As shown in FIGS. 1–3, a prosthetic limb 10 in accordance with the present invention includes a pylon assembly 12 (upright assembly) adjustably coupled to a prosthetic foot component 14 by an adjustable link plate assembly 16. The prosthetic foot 14 includes a heel/ankle portion 18 and a fore-foot portion 19. The link plate assembly 16 for adjustably coupling the prosthetic foot 14 to the pylon assembly 12 includes a dove-tail shaped anchoring member 20 and a substantially elliptical or rectangular pylon support member 22. The dove-tail shaped anchoring member 20 is positioned on a proximal surface 23 of the heel/ankle portion of the prosthetic foot. A bolt 40 (see FIG. 3), as will be discussed below, retains the dove-tail shaped anchoring member 20 to the proximal surface 23 of the prosthetic foot component 14.

The pylon support member 22 includes a corresponding, dove-tail shaped groove 26, extending lengthwise along its distal end, for receiving the dove-tail shaped anchoring member 20, thereby allowing the pylon support member 22 to slide laterally in the anterior-posterior direction with respect to the dove-tail shaped anchoring member 20 and the prosthetic foot component 14.

The pylon support member 22 includes a domed portion 28 extending proximally therefrom and a frustopyramidal boss portion 30 extending from the apex of the domed portion 28. The domed and frustopyramidal boss portions are of conventional design and a adapted to be received within the annular socket member 32 extending from a distal end of the pylon assembly 12. The annular socket member 32 includes a spherically concave distal edge 33 having substantially the same radius of curvature of the domed portion 30 of the pylon support member 22. Thus, the annular socket member 32, when seated on the domed portion 30 of the pylon support member 22, can be pivoted over and rotated upon the pylon support member. As known to those of ordinary skill in the art, the frustopyramidal boss portion 30 includes a plurality of outwardly angled faces 34 for receiving proximally angled set screws 36 extending radially inward through the annular socket member 32. Once the set screws 36 are tightened against their respective, outwardly angled faces 34 of the frustopyramidal boss portion 30, the pylon assembly 12 will be locked in the desired orientation with respect to the pylon support member 22. Accordingly, as is known to those of ordinary skill in the art, the combination of the domed and frustopyramidal boss portions 28, 30 with the annular socket member 32 provides for angular adjustments of the pylon assembly 12 with respect to the prosthetic foot 14. See also, U.S. Pat. No. 3,659,294 to Glabiszewski.

Figure 4:
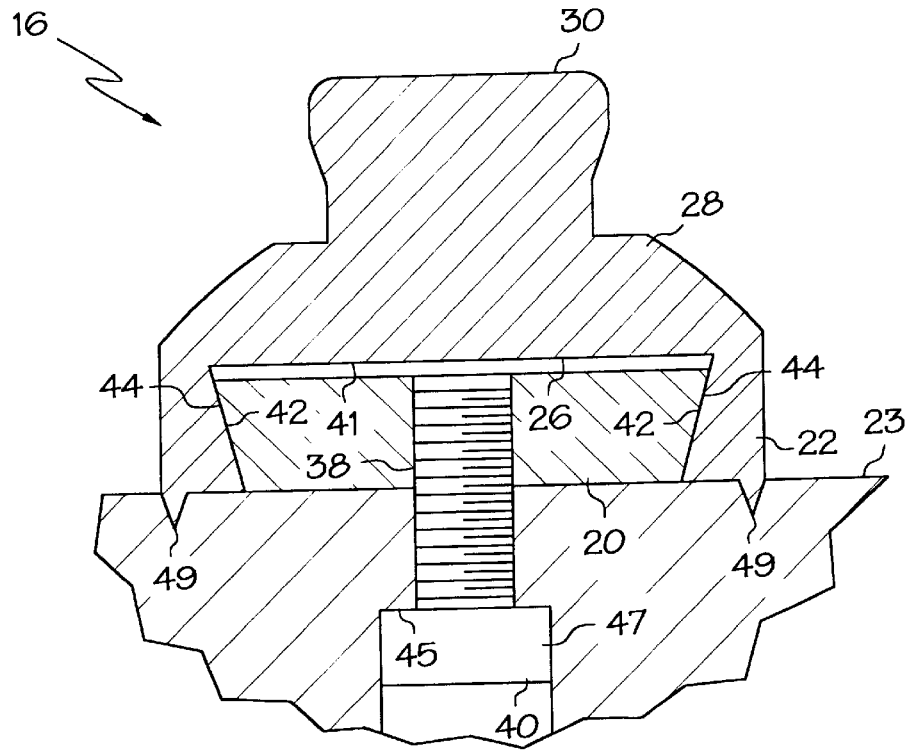
FIG. 4 is an elevational, cross-sectional view of a link plate assembly for use with the present invention, shown in a "locked" orientation.

Referring now, in particular, to FIGS. 3 and 4, the dove-tail shaped anchoring member 20 includes a threaded bore 38 extending vertically therein through a distal end thereof, which is adapted to receive a correspondingly threaded bolt 40 extending into the distal end of the dove-tail shaped anchoring member 20. The prosthetic foot 14 is conventional in design and includes a non-threaded bore 43 extending vertically therethrough, which is aligned with the threaded bore 38 of the dove-tail shaped anchoring member 20 and provides access for the prosthetist to the threaded bolt 40 from the distal end of the heel/ankle portion of the prosthetic foot 14. The non-threaded bore 43 in the prosthetic foot includes a shoulder 45 for seating a head 47 of the threaded bolt. Accordingly, as the threaded bolt 40 is extended through the bore 43 in the prosthetic foot and threaded into the threaded bore 38 in the distal end of the dove-tail shaped anchoring member 20, the shoulder 45 will prohibit the bolt 40 from translating in a proximal direction (vertically upward), and accordingly further turning of the threaded bolt 40 causes the dove-tail shaped anchoring member 20 to be drawn distally towards the prosthetic foot. This causes the dove-tail shaped anchoring member 20 to be pressed away from the pylon support member 22 (held in place vertically by the proximal surface 23), which causes the inwardly angled vertical faces 42 of the pylon support member to press against the outwardly angled faces 44 of the dove-tail shaped anchoring member, thereby inhibiting sliding of the pylon support member with respect to the dove-tail shaped anchoring member.

Further tightening of the bolt 40 will cause the entire link plate assembly 16 (including both the anchoring member 20 and pylon support member 22) to press against the proximal surface 23 of the prosthetic foot 14. The conventional prosthetic foot 14 is typically made from wood or another material having similar density and/or other characteristics. To inhibit rotation of the link plate assembly 16 with respect to the prosthetic foot 14, therefore, the pylon support member 22 includes a pair of teeth 49, extending longitudinally along the distal surface of the pylon support member, that lock into the proximal surface 23 of the prosthetic foot when the bolt 40 is tightened sufficiently.

It is noted that the vertical height of the dove-tail shaped anchoring member 20 is slightly less than the vertical height of the dove-tail shaped groove 26 in the pylon support member 22, thereby allowing the pylon support member to slide on the dove-tail shaped anchoring member when the bolt 40 is loosened.

Accordingly, to laterally adjust the prosthetic foot component 14 with respect to the pylon assembly 12, the prosthetist will merely need to loosen the bolt 40 with a tool, such as a screw-driver or a hex-wrench, extending into the bore 43 from the distal end of the prosthetic foot; make the desired lateral adjustment by sliding the prosthetic foot laterally with respect to the pylon assembly; and then tightening the bolt 40 again. Therefore, to make such an adjustment, it is not necessary for the prosthetic limb to be removed from the wearer.

As discussed above, the bolt 40 in combination with the threaded bore 38 and shoulder 45, provides a threaded coupler or press cooperative with the dove-tail shaped anchoring member to draw the inwardly angled vertical faces 42 of the pylon support member into an interference fit with the outwardly angled faces 44 of the dove-tail shaped anchoring member, thereby inhibiting sliding of the pylon support member with respect to the dove-tail shaped anchoring member.

Figure 5:
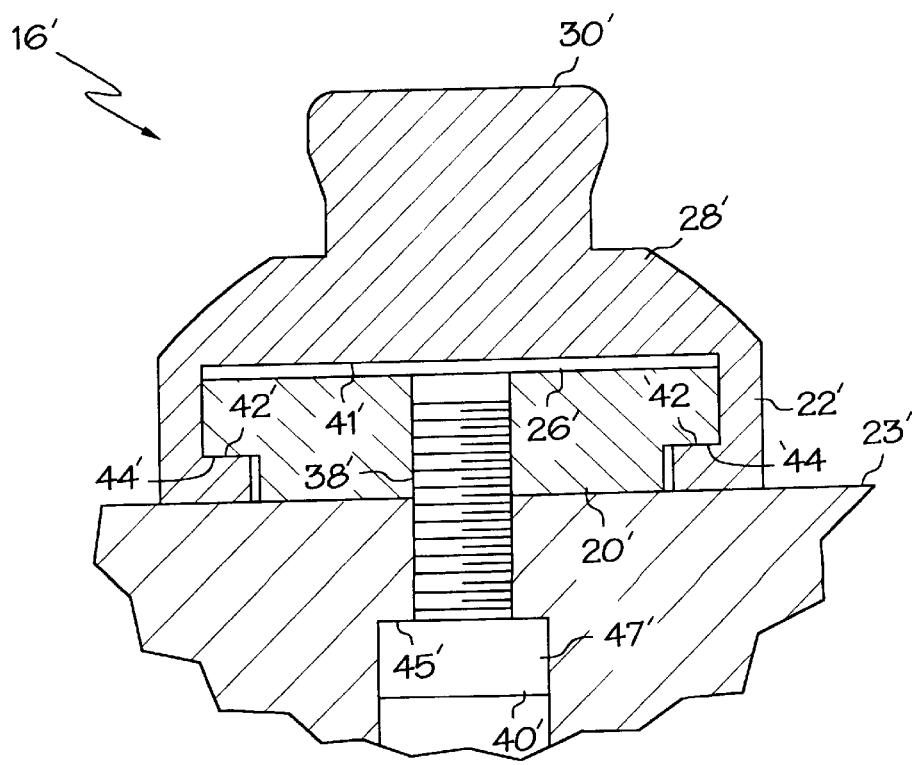
FIG. 5 is an elevational, cross-sectional view of an alternate embodiment of a link plate assembly for use with the present invention, shown in a "locked" orientation.

As shown in FIG. 5, an alternate, yet functionally similar embodiment 16' of the link plate assembly according to an aspect of the present invention includes a T-shaped anchoring member 20' and a pylon support member 22' with a corresponding, T-shaped groove 26' milled therein. Accordingly, when the bolt 40 is tightened to draw the T-shaped anchoring member 20' away from the pylon support member 22', the inwardly extending surfaces 42' of the T-shaped groove 26' press against the outwardly extending surfaces 44' of the T-shaped anchoring member 20', thereby inhibiting sliding of the pylon support member 22' with respect the T-shaped anchoring member 20'.

Figure 6:
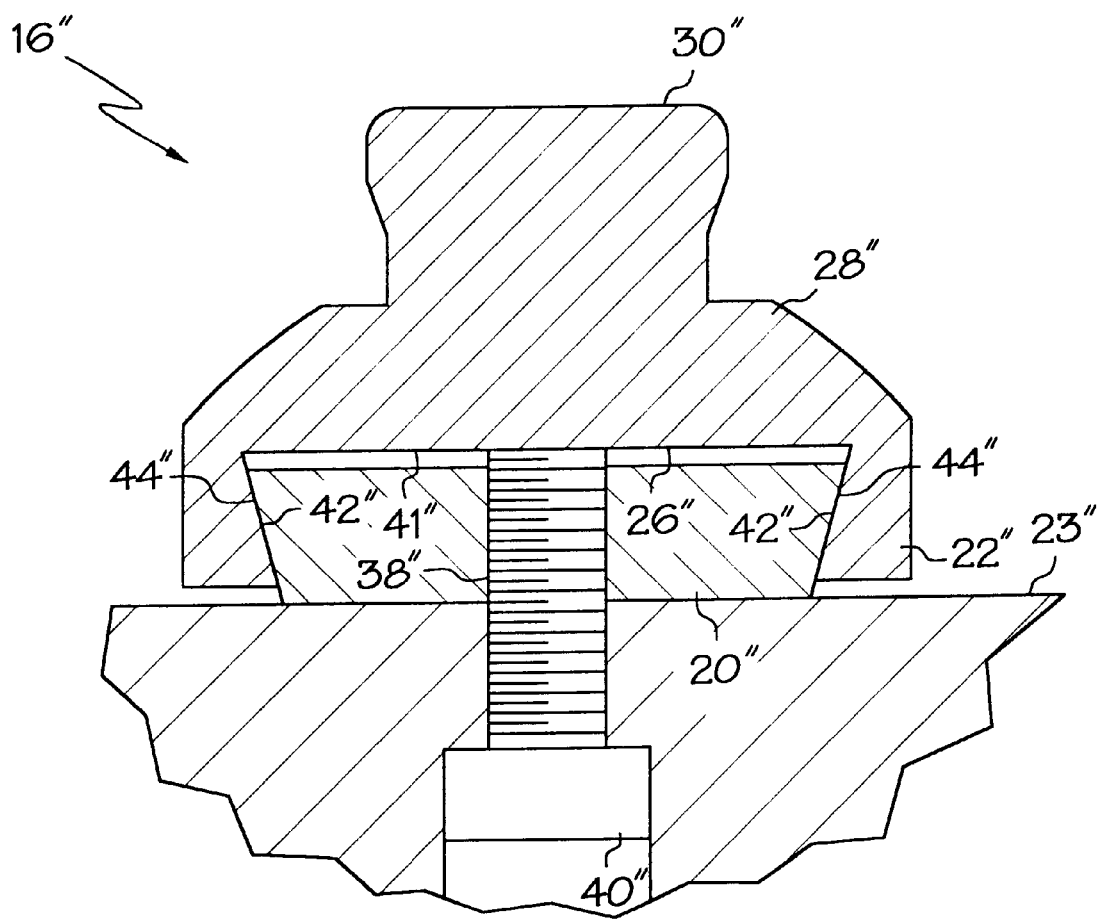
FIG. 6 is an elevational, cross-sectional view of another alternate embodiment of a link plate assembly for use with the present invention, shown in a "locked" orientation.

As shown in FIG. 6, in another alternate embodiment 16" of the present invention, the dove-tail shaped anchoring member 20" is fixedly attached to the proximal surface 23" of the prosthetic foot component and includes a threaded bore 38" extending completely therethrough. Accordingly, when the bolt 40" is turned in a direction which causes it to translate out through the proximal surface of the dove-tail shaped anchoring member to a sufficient extend so as to press against the inner distal surface 41" of the dove-tail shaped groove 26" of the pylon support member 22", the pylon support member will be forced upwardly (proximally) with respect to the dove-tail shaped anchoring member 20'. This, in turn, causes the inwardly angled faces 42" of the dove-tail shaped groove 26" to press against the outwardly angled faces 44" of the dove-tail shaped anchoring member 20", thereby locking the pylon support member 22" laterally with respect to the dove-tail shaped anchoring member 20". Thereafter, loosening the bolt 40" allows the pylon support member 22" to be laterally slidable again with respect to the dove-tail shaped anchoring member 20". In this embodiment, therefore, the bolt 40" in combination with the threaded bore 38" provides a threaded coupler or press cooperative with the dove-tail shaped anchoring member to draw the inwardly angled faces 42" of the dove-tail shaped groove 26" into an interference fit with the outwardly angled faces 44" of the dove-tail shaped anchoring member 20", thereby locking the pylon support member 22" laterally with respect to the dove-tail shaped anchoring member 20" when activated.

It will be apparent to those of ordinary skill in the art that, in addition to threaded presses discussed above, other types of mechanical presses, including presses positioned between the proximal end of the dove-tail shaped base, may be utilized with equal satisfactory results. For example, the use of a pneumatically controlled or hydraulically controlled press, or a motorized press will also fall within the scope of the present invention. For the purposes of the present disclosure of all such presses are referred to herein as "mechanical presses."

Figure 7:
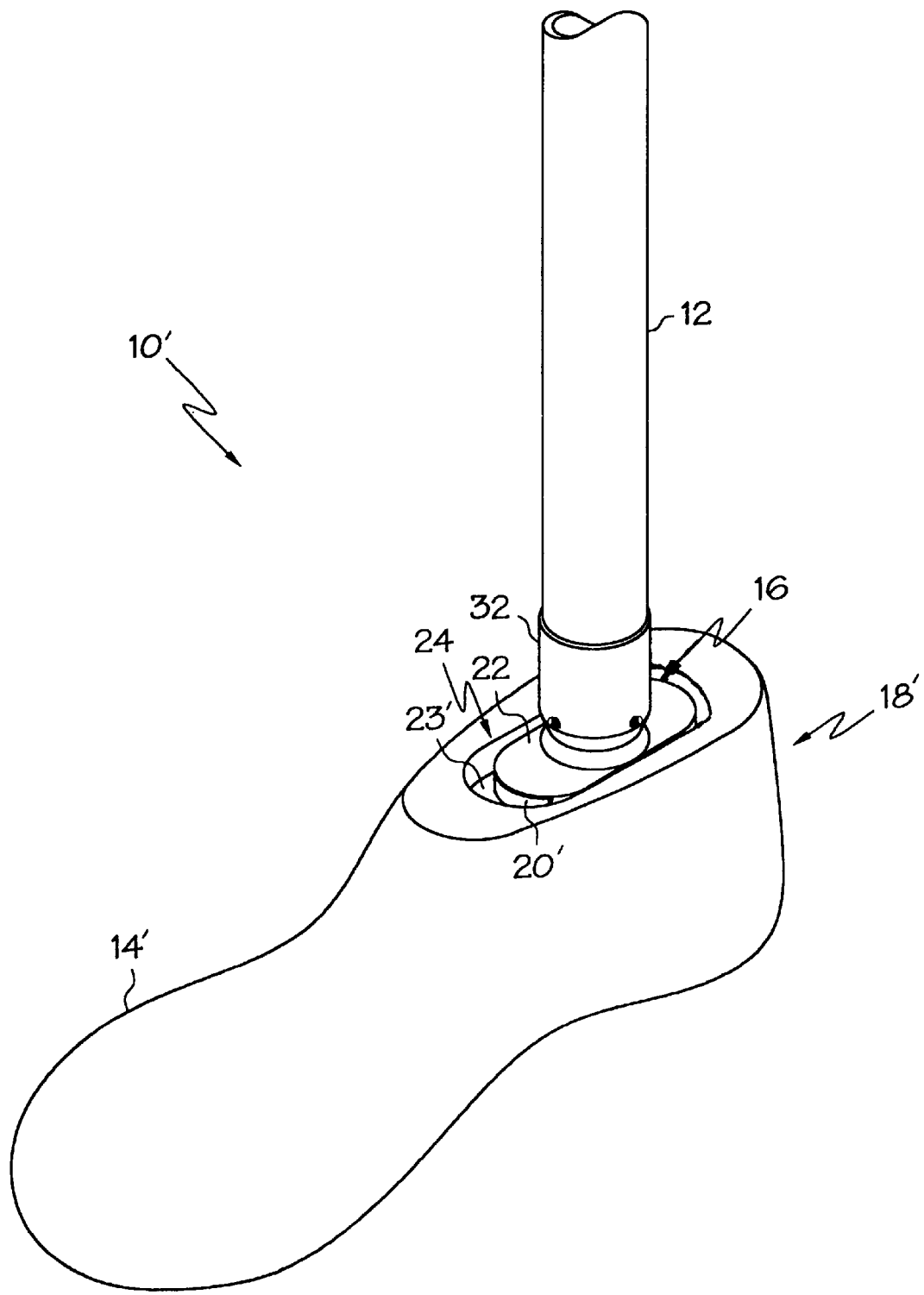
FIG. 7 is a perspective view of an alternate embodiment of a prosthetic foot component of the present invention coupled to an upright assembly of a prosthetic limb.

As shown in FIG. 7, in an alternate embodiment of the invention, the prosthetic foot 14' may be modified to include a recess 24 extending into the proximal end of the heel/ankle portion 18'. The recess 24, extending in an anterior-posterior direction, prevents rotation of the pylon support member 22 with respect to the prosthetic foot 14, while allowing for the anterior-posterior adjustments of the pylon support member 22, as will be described below. The recess 24 preferably has a width that is substantially equal to, but slightly larger than the width of the pylon support member 22, and preferably has a length that is substantially larger than the length of the pylon support member so as to allow for sufficient adjustability of the pylon support member with respect to the prosthetic foot 14.

Accordingly, as shown with respect to the embodiments of FIGS. 1–7, it is within the scope of the present invention to provide a link plate assembly for adjustably coupling a first prosthetic limb component, such as a prosthetic foot, to a second prosthetic limb component, such as a pylon assembly, that comprises: (a) an anchoring member; and (b) a pylon support member having an upper end adapted to receive and couple to a pylon assembly of the prosthetic limb; where one of the anchoring member and the pylon support member includes a projection extending between the top end of the anchoring member and the bottom end of the pylon support member, and the projection includes a pair of parallel, outwardly angled faces; where the other one of the anchoring member and the pylon support member includes a groove shaped to slidingly receive the projection, and the groove includes a pair of parallel, inwardly angled faces; where the projection is slidingly received within the groove and the inwardly angled faces of the groove are juxtaposed with the outwardly angled faces of the projection; and where the link plate assembly further comprises, (c) a mechanical press cooperative with the anchoring member and the pylon support member to draw the inwardly angled faces into an interference fit with the outwardly angled faces, thereby inhibiting sliding of the pylon support member with respect to the anchoring member. Preferably the outwardly and inwardly extending faces are angled at an acute angle (as shown in FIGS. 4 and 6) or a perpendicular angle (as shown in FIG. 5); however, it is within the scope of the invention that they may also be angled at an obtuse angle.

While the forms of apparatus herein described constitute preferred embodiments of the present invention, it is to be understood that the invention is not limited to these precise forms of apparatus, and that variations can be made therein without departing from the scope of the invention. For example, while the preferred means for coupling the link plate assembly 16 to the pylon assembly 12 is the combination of the domed and frustopyramidal boss portions 28, 30 with the annular socket member 32, it is within the scope of the invention that other means for coupling the link plate assembly 16 to the upright assembly 12 may also be used.

What is claimed is:

1. A prosthetic foot comprising:
    a prosthetic foot member having a fore-foot portion and a heel/ankle portion, the heel/ankle portion having a proximal surface;
    a dove-tail shaped anchoring member positioned on the proximal surface of the heel/ankle portion of the prosthetic foot member, the dove-tail shaped anchoring member having a proximal face and a pair of outwardly angled vertical faces;
    a pylon support member having a proximal end adapted to receive and couple to a pylon component of a prosthetic limb, a distal face opposing the proximal end, and a dove-tail shaped groove extending into the distal face, the dove-tail shaped groove having a pair of inwardly angled vertical faces and an inner-distal face, the dove-tail shaped anchoring member being slidingly received within the dove-tail shaped groove of the pylon support member; and
    a threaded coupler cooperating with the dove-tail shaped anchoring member to draw the inwardly angled vertical faces of the pylon support member into an interference fit with the outwardly angled faces of the dove-tail shaped anchoring member, thereby inhibiting sliding of the pylon support member with respect to the dove-tail shaped anchoring member.

2. The prosthetic foot of claim 1, wherein the threaded coupler includes:

a threaded bore extending vertically into a distal end of the dove-tail shaped anchoring member;

an aperture extending into the proximal surface of the prosthetic foot member and aligned with the threaded bore of the dove-tail shaped anchoring member, the aperture including a shoulder extending radially into the aperture; and a threaded bolt positioned within the aperture of the prosthetic foot member and threaded upwardly into the threaded bore of the dove-tail shaped anchoring member, the threaded bolt including a head abutting a distal side of the shoulder.

3. The prosthetic foot of claim 2, wherein the prosthetic foot member includes an opening extending vertically through a distal end of the heel/ankle portion, aligned with the aperture, and providing access to the threaded bolt from the distal end of the heel/ankle portion.

4. The prosthetic foot of claim 3, wherein the dove-tail shaped groove and the dove-tail shaped anchoring member extend substantially in the anterior-posterior direction, thereby providing anterior-posterior adjustments for the prosthetic foot with respect to a wearer of the prosthetic foot.

5. The prosthetic foot of claim 4, wherein the pylon support member includes a tooth extending from a distal surface of the pylon support member and engaging the proximal surface of the heel/ankle portion of the prosthetic foot upon tightening of the threaded bolt.

6. The prosthetic foot of claim 4, wherein the prosthetic foot member includes a recess formed in the proximal surface of the heel/ankle portion, the recess seating the dove-tail shaped anchoring member therein and slidingly receiving the pylon support member therein.

7. The prosthetic foot of claim 6, wherein:

the proximal end of the pylon support member includes a domed portion and a frustopyramidal boss portion extending from the domed portion; and the pylon support member includes a substantially rectangular or elliptical plate portion, seating the domed portion, and the dove-tail shaped groove extends lengthwise along the plate portion.

8. The prosthetic foot of claim 7, wherein the recess has a width substantially equal to, but slightly greater than the width of the elliptical plate portion, and has a length substantially greater than the length of the elliptical plate portion.

9. The prosthetic foot of claim 1, wherein the dove-tail shaped anchoring member is mounted to the proximal surface of the heel/ankle portion and the threaded coupler includes:

a threaded bore extending vertically through the dove-tail shaped anchoring member, and a correspondingly threaded bolt extending upwardly through the threaded bore.

10. The prosthetic foot of claim 9, wherein the prosthetic foot member includes an opening extending vertically through a distal end of the heel/ankle portion, aligned with the threaded bore of the dove-tail shaped anchoring member, and providing access to the threaded bolt from the distal end of the heel/ankle portion.

11. The prosthetic foot of claim 9, wherein the pylon support member includes a tooth extending from a distal surface of the pylon support member and engaging the proximal surface of the heel/ankle portion of the prosthetic foot upon tightening of the threaded bolt.

12. A prosthetic foot comprising:

a prosthetic foot member having a fore-foot portion and a heel/ankle portion, the heel/ankle portion having a proximal surface;

an anchoring member positioned on the proximal surface of the heel/ankle portion of the prosthetic foot member, the anchoring member having a proximal face, a pair of outwardly angled vertical faces;

a pylon support member having a proximal end adapted to receive and couple to a pylon component of a prosthetic limb, a distal face opposing the proximal end, and a groove extending into the distal face, the groove having a pair of inwardly angled vertical faces and an inner-distal face, the anchoring member being slidingly received within the groove of the pylon support member; and a threaded press cooperative with the anchoring member and the pylon support member to force the inner-distal face of the pylon support member and the proximal face of the anchoring member away from one another when activated, whereupon activation of the threaded press, the inner-distal face of the pylon support member and the proximal face of the anchoring member are forced away from one another, causing the inwardly angled vertical faces of the pylon support member to press against the outwardly angled faces of the anchoring member, thereby inhibiting sliding of the pylon support member with respect to the anchoring member.

13. A prosthetic foot comprising:

a prosthetic foot member having a fore-foot portion and a heel/ankle portion, the heel/ankle portion having a proximal surface;

an anchoring member positioned on the proximal surface of the heel/ankle portion of the prosthetic foot member, the anchoring member having proximal end; and a pylon support member having a proximal end adapted to receive and couple to a pylon component of a prosthetic limb, and a distal face opposing the proximal end;

wherein one of the anchoring member and the pylon support member includes a projection extending between the proximal end of the anchoring member and the distal end of the pylon support member, the projection including a pair of parallel, outwardly angled faces;

wherein the other one of the anchoring member and the pylon support member includes a groove shaped to slidingly receive the projection, the groove including a pair of parallel inwardly angled faces;

wherein the projection is slidingly received within the groove and the inwardly angled faces of the groove are juxtaposed with the outwardly angled faces of the projection; and wherein the prosthetic foot further comprises a means for selectively pressing the inwardly angled faces of the groove against the outwardly angled faces of the projection, thereby inhibiting sliding of the pylon support member with respect to the anchoring member.

14. A prosthetic foot comprising:

a prosthetic foot member having a fore-foot portion and a heel/ankle portion, the heel/ankle portion having a proximal surface;

a base member positioned on the proximal surface of the heel/ankle portion of the prosthetic foot member, the base member having proximal end; and a pylon support member having a proximal end adapted to receive and couple to a pylon component of a prosthetic limb, a distal face opposing the proximal end;

wherein one of the base member and the pylon support member includes a projection extending between the proximal end of the base member and the distal end of the pylon support member, the projection including a pair of parallel outwardly angled faces;

wherein the other one of the base member and the pylon support member includes a groove shaped to slidingly receive the projection, the groove including a pair of parallel, inwardly angled faces;

wherein the projection is slidingly received within the groove and the inwardly angled faces of the groove are juxtaposed with the outwardly angled faces of the projection; and wherein the prosthetic foot further comprises a mechanical press cooperative with the base member and the pylon support member to force the pylon support member and the base member away from one another when activated, which in turn draws the inwardly angled faces into an interference fit with the outwardly angled faces, thereby inhibiting sliding of the pyramid member with respect to the base member.

15. A link plate assembly for adjustably coupling a first prosthetic limb component to a second prosthetic limb component, comprising:

an anchoring member having a top end the anchoring member being adapted to be attached to a first prosthetic limb component; and a pylon coupling member having an upper end adapted to receive and couple to a pylon component of a prosthetic limb and a bottom end opposing the upper end;

wherein one of the anchoring member and the pylon coupling member includes a projection extending between the top end of the anchoring member and the bottom end of the pylon coupling member, the projection including a pair of parallel, outwardly angled faces;

wherein the other one of the anchoring member and the pylon coupling member includes a groove shaped to slidingly receive the projection, the groove including a pair of parallel, inwardly angled faces;

wherein the projection is slidingly received within the groove and the inwardly angled faces of the groove are juxtaposed with the outwardly angled faces of the projection; and wherein the link plate assembly further comprises a threaded press cooperating with the anchoring member and the pylon coupling member, whereupon activation of the threaded press, the pylon coupling member and the anchoring member are forced away from one another, causing the inwardly angled faces to draw into an interference fit with the outwardly angled faces, thereby inhibiting sliding of the pylon coupling member with respect to the anchoring member.

16. The link plate assembly of claim 15, wherein the threaded press includes a threaded bore extending vertically into the anchoring member and a correspondingly threaded bolt positioned within the threaded bore.

17. A link plate assembly for adjustably coupling a first prosthetic limb component to a second prosthetic limb component, comprising:

a dove-tail shaped anchoring member having a top face, and a pair of outwardly angled vertical faces the anchoring member being adapted to be attached to a first prosthetic limb component;

a pylon coupling member having an upper end adapted to receive and couple to a pylon component of a prosthetic limb, a bottom face opposing the upper end, and a dove-tail shaped groove extending into the bottom face, the dove-tail shaped groove having a pair of inwardly angled vertical faces and an inner-bottom face, the dove-tail shaped anchoring member being slidingly received within the dove-tail shaped groove of the pylon coupling member; and a threaded press cooperating with the dove-tail shaped anchoring member and the pylon coupling member to draw the inwardly angled vertical faces of the pylon coupling member into an interference fit with the outwardly angled faces of the dove-tail shaped anchoring member, thereby inhibiting sliding of the pylon coupling member with respect to the dove-tail shaped anchoring member.

18. The link plate assembly of claim 17, wherein the threaded press includes a threaded bore extending vertically into the dove-tail shaped anchoring member and a correspondingly threaded bolt positioned within the threaded bore.

19. The link plate assembly of claim 17, wherein:

the upper end of the pylon coupling member includes a domed portion and a frustopyramidal boss portion extending from the domed portion;

the pylon coupling member includes a substantially rectangular or elliptical plate portion, seating the domed portion; and the dove-tail shaped groove extends lengthwise along the plate portion.

20. The link plate assembly of claim 17, wherein the pylon coupling member includes a tooth extending from the bottom face of the pylon coupling member.

21. A prosthetic limb comprising:

a prosthetic foot;

a pylon support member slidably mounted to a proximal end of the prosthetic foot, the pylon support member having a domed portion and a frustopyramidal boss portion extending from the domed portion, the frustopyramidal boss portion having at least two opposing, outwardly angled faces, wherein the pyramid plate is slidable in the anterior-posterior direction;

an upright assembly adapted to extend from a distal end of a patient's residual limb, the upright assembly including an annular socket member at a distal end of the upright assembly, the annular socket member including at least two diametrically opposed set screws extending radially into a central bore of the annular socket member, the set screws being angled proximally, the frustopyramidal boss portion of the pylon support member being received within the central bore of the annular socket member and the set screws being tightened against the opposing faces of the frustopyramidal boss portion, thereby coupling the upright assembly to the pylon support member and prosthetic foot; and a releasable lock, adapted to inhibit sliding of the pylon support member with respect to the prosthetic foot in the anterior-posterior direction when in a locked orientation.

22. The prosthetic limb of claim 21, wherein:

the prosthetic foot includes a dove-tail shaped projection positioned on a proximal surface of the prosthetic foot;

the pylon support member includes a dove-tail shaped groove extending into a distal surface of the pylon support member;

the dove-tail shaped projection of the prosthetic foot is slidably received within the dove-tail shaped groove of the pylon support member.

23. The prosthetic limb of claim 22, wherein:

the dove-tail shaped projection of the prosthetic foot includes a pair of outwardly angled vertical faces;

the dove-tail shaped groove includes a corresponding pair of inwardly angled vertical faces, juxtaposed the outwardly angled vertical faces of the dove-tail shaped projection; and the releasable lock includes a threaded bolt extending from the proximal surface of the prosthetic foot and into a correspondingly threaded bore extending into a distal end of dove-tail shaped projection, whereupon turning of the bolt pulls the dove-tail shaped projection distally with respect to the pylon support member, and in turn causes the outwardly angled vertical faces of the dove-tail shaped projection to draw into an interference fit with the inwardly angled vertical faces of the dove-tail shaped projection, thereby inhibiting sliding of the pylon support member with respect to the prosthetic foot in the anterior-posterior direction.

24. The prosthetic limb of claim 23, wherein the prosthetic foot includes an opening extending vertically through a distal end of the prosthetic foot and providing access to the threaded bolt from the distal end of the prosthetic foot.

* * * * *